(12) United States Patent
Hirooka

(10) Patent No.: US 8,406,376 B2
(45) Date of Patent: Mar. 26, 2013

(54) RADIOGRAPHIC APPARATUS

(75) Inventor: Ken Hirooka, Uji (JP)

(73) Assignee: Shimadzu Corporation, Kyoto (JP)

( * ) Notice: Subject to any disclaimer, the term of this patent is extended or adjusted under 35 U.S.C. 154(b) by 273 days.

(21) Appl. No.: 12/979,152

(22) Filed: Dec. 27, 2010

(65) Prior Publication Data

US 2011/0158388 A1 Jun. 30, 2011

(30) Foreign Application Priority Data

Dec. 29, 2009 (JP) ................................ 2009-299071

(51) Int. Cl.
*H05G 1/64* (2006.01)
(52) U.S. Cl. ....................................... 378/98.4
(58) Field of Classification Search .................... 378/62, 378/98.4, 98.8, 154
See application file for complete search history.

(56) References Cited

U.S. PATENT DOCUMENTS 6,157,700 A 12/2000 Sako
7,474,774 B2 1/2009 Inoue

FOREIGN PATENT DOCUMENTS

| JP | 11-285493 A | 10/1999 |
| JP | 2001-346795 A | 12/2001 |
| JP | 2005-52553 A | 3/2005 |

*Primary Examiner* — Courtney Thomas
(74) *Attorney, Agent, or Firm* — Cheng Law Group, PLLC

(57) ABSTRACT

An air grid is constructed such that absorbing foil strips, which absorb scattered X-rays, are arranged in a direction parallel to the direction of rows of detecting elements, and that spacing between adjacent shadows among shadows of the absorbing foil strips formed on a flat panel X-ray detector (FPD) as a result of the absorbing foil strips absorbing X-rays is larger than spacing between pixels forming an X-ray image. An image data acquiring unit, a transmittance smoothing unit, a grid data acquiring unit, a shadowless pixel calculating unit, a shadow total quantity calculating unit, a transmittance correcting unit and an X-ray image acquiring unit are provided to remove the shadows with high accuracy by using corrected image data (X-ray transmittances) which constitutes a profile of shadows occurring at an actual time of X-ray imaging of a subject.

15 Claims, 11 Drawing Sheets image data

RADIOGRAPHIC APPARATUS

BACKGROUND OF THE INVENTION (1) Field of the Invention

This invention relates to a radiographic apparatus using a flat panel radiation detector, and more particularly to a technique for removing scattered radiation.

(2) Description of the Related Art

Description will be made taking X-rays as an example of radiation. In many X-ray imaging apparatus, a scattered X-ray removing grid (scattered radiation removing device) is used to prevent a lowering of image quality due to scattered X-rays (hereinafter referred to simply as "scattered rays") generated when X-rays are transmitted through a subject to be imaged. An ordinary grid is formed of an alternate arrangement of absorbing foil strips which absorb the scattered rays and intermediate layers which transmit the X-rays. However, when such a grid is used, the structure of the grid (absorbing foil strips) will be projected to as shadows. It is therefore necessary to remove the shadows of the grid.

A commonly used grid has a fine structure, and the shadows of the grid are removed by spatial frequency processing or the like. The shadows of the grid can be removed by developing data to a frequency domain by Fourier transform, and restoring the data by inverse Fourier transform after removing specific grid frequencies (see Japanese Unexamined Patent Publication No. 2005-052553, Japanese Unexamined Patent Publication No. 2001-346795 and Japanese Unexamined Patent Publication H11-285493, for example).

An air grid having a higher X-ray transmittance than the commonly used grid has been devised recently. The air grid has voids serving as the above-mentioned intermediate layers, which easily transmit X-rays compared with the intermediate layers formed of aluminum, an organic material or the like. However, this air grid has a larger internal structure than the usual grid, which makes it difficult to remove the shadows by the above-noted spatial frequency processing.

Then, it is necessary to remove the shadows in real space, instead of using the Fourier transform or other measure. The principle of removing the shadows in real space will be described with reference to FIG. 3. As shown in FIG. 3, an air grid 6 has absorbing foil strips 6a arranged with intermediate layers 6c which are voids inserted in between. The absorbing foil strips 6a are thin metallic foil strips formed of lead, for example. The air grid 6 is disposed adjacent an incidence plane of a flat panel (two-dimensional) X-ray detector (FPD) with detecting elements arranged in rows and columns (i.e. in a two-dimensional matrix form). The direction of arrangement of the absorbing foil strips 6a is parallel to the rows of the detecting elements. Spacing between adjacent shadows is larger than spacing of pixels forming an X-ray image.

The absorbing foil strips 6a have a sufficiently smaller width than the pixels. The material used for these foil strips has a very low X-ray transmittance. Therefore, the X-ray transmittance can be expressed by a ratio in the following equation (1), using the area of a portion without shadows and the area of a portion with shadows (area of shadows):

$$\text{X-ray transmittance} = (\text{pixel area} - \text{shadow area})/\text{pixel area} \quad (1)$$

In the above equation (1), the numerator (pixel area–shadow area) at the right side is the area of the portion without shadows.

A method of removing the shadows of the air grid 6 (shadows of the absorbing foil strips 6a) may assume that the shadow portion also has received incident X-rays of luminance of the non-shadow portion (portion without shadows) of the same pixel. Therefore, a pixel value after shadow removal by dividing a pixel value (in the shadow portion) at the time of image pickup by an X-ray transmittance at the pixel concerned, as in the following equation (2):

$$\text{pixel value after shadow removal} = \text{pixel value at image pickup time}/\text{X-ray transmittance} \quad (2)$$

Thus, the shadows can be removed by first deriving an X-ray transmittance from equation (1) above, and deriving a pixel value after shadow removal from equation (2) above using the X-ray transmittance and the pixel value at the time of image pickup.

In the principle of removing the shadows in real space, the shadows are removed using what is shown in equation (1) above. In practice, an image of the air grid alone is picked up in advance of X-ray imaging. That is, grid data is first acquired by X-raying the air grid without a subject to be imaged (i.e. in the presence of the air grid only), and thereafter image pick-up data is acquired by carrying out actual X-raying in the presence of the subject to be imaged and the air grid.

The grid data is acquired in advance of actual X-ray imaging, and X-ray transmittances are derived from the grid data by the equation (1) above. However, such X-ray transmittances cannot be applied directly to actual image pick-up data by using equation (2) above. The reasons are as follows:

(A) In some cases, a shadow straddles a plurality of pixels. Specifically, as shown in FIG. 14A, a shadow 32 straddles two adjacent pixels 31. When a movement of the focal position of (the vessel) of an X-ray tube moves also the shadow 32 as shown in FIG. 14B, the quantities of the shadow 32 on the pixels 31 will change. The focal position of the X-ray tube is changeable because, in spite of the condition that the X-ray focal point of the X-ray tube, the grid and the FPD ought to be in a fixed relationship, when the X-ray tube, FPD, etc. are moved together, the movement will cause a shifting of the positional relationship between the X-ray focal point, grid and FPD.

For example, when this image pickup unit is applied to an actual medical apparatus, such as an apparatus used for cardiovascular diagnosis (CVS: cardiovascular system), a C-arm is usually used to conduct diagnosis (that is, X-ray image pickup). The C-arm literally has a curved shape of character "C". The C-arm supports a radiation emitting device such as an X-ray tube at one end thereof, and an FPD at the other end. When the C-arm is rotated along the direction of its curve, the X-ray tube and FPD revolve with this rotation. During such movement, X-raying is carried out with the X-ray tube emitting X-rays, and the FPD detecting the X-rays. At the time of picking up an image of a patient, in spite of the condition that the X-ray focal point of the X-ray tube, the grid and the FPD ought to be in a fixed relationship, the rotation of the C-arm and the like will cause a shifting of the positional relationship between the X-ray focal point, grid and FPD. Especially, the shifting of the positional relationship between the X-ray focal point, grid and FPD easily occurs under the weight of the FPD and X-ray tube. It is not realistic from the hardware point of view to fix the positional relationship.

(B) When imaging a human body such as a patient, it is impossible to carry out inverse calculations from a ratio of shadows in grid data obtained only from the grid as a result of part of scattered rays from the patient passing through the grid. Calculations based on the ratio are possible only with part of direct X-rays (hereinafter referred to simply as "direct rays").

SUMMARY OF THE INVENTION

This invention has been made having regard to the state of the art noted above, and its object is to provide a radiographic apparatus which can remove shadows with high accuracy.

The above object is fulfilled, according to this invention, by a radiographic apparatus for obtaining a radiological image, comprising a scattered radiation removing device for removing scattered radiation; and a radiation detecting device having a plurality of detecting elements arranged in rows and columns for detecting radiation; the scattered radiation removing device being constructed to have absorbing layers for absorbing the scattered radiation, which layers are arranged in a direction parallel to at least one of directions of rows and columns of the detecting elements, such that spacing between adjacent shadows among shadows of the absorbing layers formed on the radiation detecting device as a result of the absorbing layers absorbing the radiation is larger than spacing between pixels forming the radiological image; the apparatus further comprising a first image data acquiring device for acquiring image data in presence of a subject to be imaged and the scattered radiation removing device; an image data smoothing device for smoothing the image data acquired by the first image data acquiring device, along a direction of extension of the absorption layers; a grid data acquiring device for acquiring grid data in absence of the subject and in presence of the scattered radiation removing device; a shadowless pixel calculating device for obtaining pixels without shadows based on the shadows in the grid data acquired by the grid data acquiring device; a shadow total quantity calculating device for calculating a total quantity of shadows per absorbing layer based on positions of the pixels without shadows obtained by the shadowless pixel calculating device; an image data correcting device for correcting the image data smoothed by the image data smoothing device, based on the total quantity of shadows per absorbing layer calculated by the shadow total quantity calculating device; and a second image data acquiring device for determining data after shadow removal based on the image data corrected by the image data correcting device and the image data acquired by the first image data acquiring device, and acquiring the data after shadow removal as final image data.

[Functions and Effects] According to the radiographic apparatus of this invention, the scattered radiation removing device is constructed such that the absorbing layers, which absorb scattered radiation, are arranged in a direction parallel to at least one of the directions of rows and columns of detecting elements, and that the spacing between adjacent shadows among the shadows of the absorbing layers formed on the radiation detecting device as a result of the absorbing layers absorbing radiation is larger than the spacing between the pixels forming the radiological image. With this construction, pixels without shadows (shadowless pixels) appear in every row or column of detecting elements parallel to the direction of arrangement of the absorbing layers. Therefore, the grid data acquiring device acquires grid data in the absence of a subject and in the presence of the scattered radiation removing device, and the shadowless pixel calculating device determines pixels without shadows based on the shadows in the grid data acquired by the grid data acquiring device. At this time, the pixels without shadows which actually appear, and the pixels without shadows determined are substantially in agreement. The shadow total quantity calculating device calculates a total quantity of shadows per absorbing layer, based on the pixels without shadows provided by the above shadowless pixel calculating device. That is, the quantity of blocked radiation in enclosed areas including the shadowless pixels can be regarded as the total quantity of shadows per absorbing layer.

On the other hand, the first image data acquiring device acquires image data in the presence of the subject and scattered radiation removing device. The image data smoothing device smoothes the image data acquired by the first image data acquiring device along the direction of extension of the absorbing layers. Consequently, the influence of the subject is canceled from the image data smoothed by the image data smoothing device, and only the profile of shadows having a substantially constant value remains therein. Therefore, the image data smoothed by the image data smoothing device includes only the profile of shadows, with the influence of the subject canceled, while retaining the data of the subject.

Even when a shadow straddles a plurality of pixels or the shadow position moves relative to the pixels, the total quantity of shadows per absorbing layer can be regarded as constant. So, from the total quantity of shadows per absorbing layer provided by the shadow total quantity calculating device, and based on the total quantity of shadows, the image data correcting device corrects the image data smoothed by the image data smoothing device. This correction can cancel the disturbance by the subject, to provide a profile of shadows at an actual time of radiological image pickup of the subject. Therefore, even when a shadow straddles a plurality of pixels or the shadow position moves relative to the pixels, the second image data acquiring device can determine data after shadow removal, based on the image data corrected by the above image data correcting device and the image data acquired by the above first image data acquiring device, and acquire the data after shadow removal as final image data. As a result, the shadow removal can be carried out with high accuracy by using the corrected image data which is the profile of shadows at an actual time of radiological image pickup of the patient.

In one example of the invention described above, the radiographic apparatus further comprises a pixel classifying device for classifying pixels in the image data acquired by the first image data acquiring device, into pixels corresponding to the pixels without the shadows in the grid data obtained by the shadowless pixel calculating device, and other pixels; a pixel value interpolating device for interpolating pixel values of the other pixels, based on pixel values of the pixels corresponding to the pixels without the shadows in the grid data, among the pixels classified by the pixel classifying device; and a provisional transmittance calculating device for provisionally calculating transmittances of the radiation based on the pixel values of the pixels in the image data acquired by the first image data acquiring device and the pixel values interpolated by the pixel value interpolating device; wherein the image data smoothing device is arranged to smooth the transmittances of the radiation in the image data provisionally calculated by the provisional transmittance calculating device; the image data correcting device is arranged to correct the transmittances of the radiation in the image data smoothed by the image data smoothing device based on the total quantity of shadows; and the second image data acquiring device is arranged to determine pixel values after shadow removal based on the transmittances of the radiation in the image data corrected by the image data correcting device and pixel values in the image data acquired by the first image data acquiring device, and to acquire the radiological image with an arrangement of the pixel values after shadow removal as final image data.

In the above example, transmittances of the radiation are specified in the image data acquired by the first image data acquiring device, and the image data smoothing device and image data correcting device carry out processes on the transmittances of the radiation, respectively. For this purpose, the transmittances of the radiation are determined provisionally.

First, the pixel classifying device classifies the pixels in the image data acquired by the first image data acquiring device, into pixels corresponding to the pixels without shadows in the grid data determined by the shadowless pixel calculating device and the other pixels. Through this classification, the shadowless pixels (pixels without shadows) in the grid data can be applied to the pixels in the image data corresponding to the shadowless pixels. Then, based on the pixel values of the pixels corresponding to the pixels without shadows in the grid data, among the pixels classified by the pixel classifying device, the pixel value interpolating device interpolates pixel values of the other pixels. That is, when an assumption is made that variations of transmittance of the radiation in the subject are not so fine (in the direction of arrangement of the absorbing layers) as the spacing of the pixels (pixel pitch), the pixels in the image data corresponding to the pixels without shadows in the grid data are linked together by interpolating the pixel values of the other pixels.

Then, based on the pixel values of the pixels in the image data acquired by the first image data acquiring device (i.e. actual pixel values obtained by image pickup) and the pixel values interpolated by the pixel value interpolating device, the provisional transmittance calculating device provisionally calculates transmittances of the radiation. That is, differences between the actual pixel values acquired by image pickup and the interpolated pixel values are regarded as results of radiation blocking by the absorbing layers, which enables a direct estimation of transmittances of the radiation in the pertinent portions.

However, since the transmittances of the radiation are obtained based on the actual pixel values acquired by image pickup and the interpolated pixel values, it is clear that, when the pixel values in the original image data are divided by the transmittances of the radiation determined in this way, the results are the same as the interpolated pixel values. Therefore, by regarding the obtained transmittances of the radiation as provisional transmittances, the image data smoothing device smoothes the transmittances of the radiation in the image data provisionally obtained by the provisional transmittance calculating device. The image data correcting device corrects the transmittances of the radiation in the image data smoothed by the image data smoothing device, based on the total quantity of shadows. Based on the transmittances of the radiation in the image data corrected by the image data correcting device, and the pixel values in the image data acquired by the first image data acquiring device, the second image data acquiring device can calculate pixel values after shadow removal, and acquire a radiological image having an arrangement of the pixel values after shadow removal, as final image data. As a result, the shadow removal can be carried out with high accuracy by using the corrected transmittances of the radiation which constitute a profile of shadows at an actual time of radiological image pickup of the subject.

Preferably, the above invention provides a scattered component removal processing device, as described hereinafter, in case part of the scattered radiation from the subject pass through the scattered radiation removing device, thus failing to be removed by the scattered radiation removing device.

That is, the radiographic apparatus further comprises a scattered component removal processing device for removing, by arithmetic operation, scattered radiation components of the image data acquired by the first image data acquiring device, which components have failed to be removed by the scattered radiation removing device, wherein the second image data acquiring device is arranged to acquire the final image data based on the image data from which the scattered radiation components have been removed by the scattered component removal processing device.

The scattered radiation components are removed by arithmetic operation as above, and the image data acquired by the first image data acquiring device is replaced with the image data from which the scattered radiation components have been removed by the scattered component removal processing device. Thus, the shadow removal can be carried out with high accuracy, while removing the scattered radiation components.

To summarize the above, according to the radiographic apparatus of this invention, the scattered radiation removing device is constructed such that the absorbing layers, which absorb scattered radiation, are arranged in a direction parallel to at least one of the directions of rows and columns of detecting elements, and that the spacing between adjacent shadows among the shadows of the absorbing layers formed on the radiation detecting device as a result of the absorbing layers absorbing radiation is larger than the spacing between the pixels forming a radiological image. A first image data acquiring device, an image data smoothing device, a grid data acquiring device, a shadowless pixel calculating device, a shadow total quantity calculating device, an image data correcting device and a second image data acquiring device are provided to remove the shadows with high accuracy by using corrected image data which constitutes a profile of shadows occurring at an actual time of radiological image pickup of a subject.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

DESCRIPTION OF THE PREFERRED EMBODIMENTS

A preferred embodiment of this invention will be described in detail hereinafter with reference to the drawings.

Figure 1:
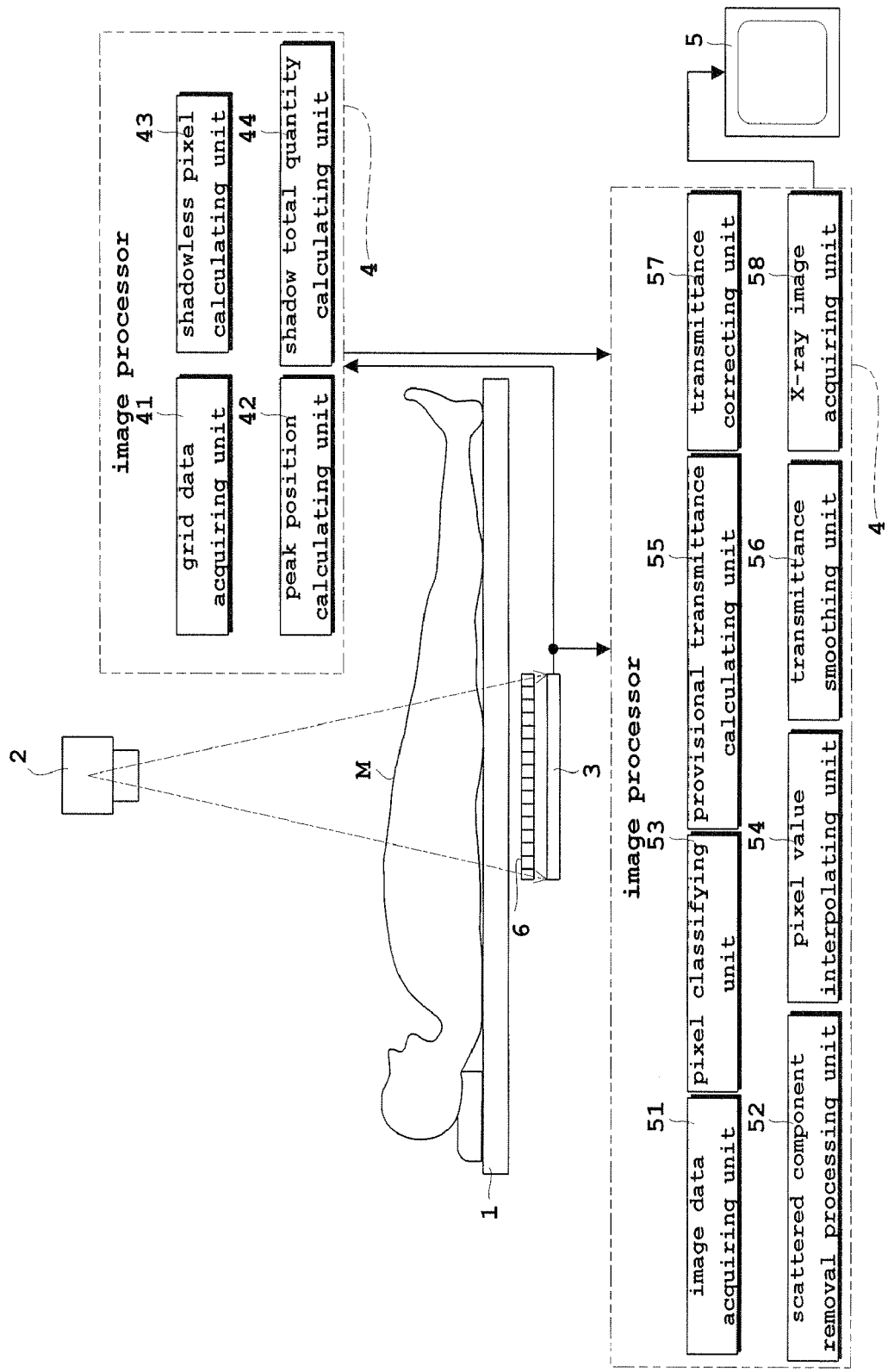
FIG. 1 is a block diagram of an X-ray imaging apparatus according to this invention.
Figure 2:
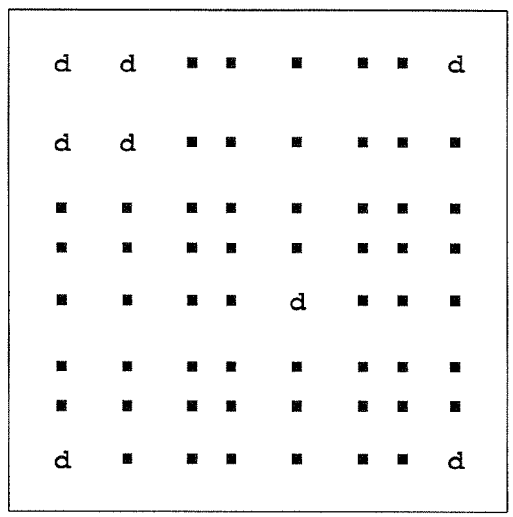
FIG. 2 is a schematic view of a detecting plane of a flat panel X-ray detector (FPD)
Figure 3:
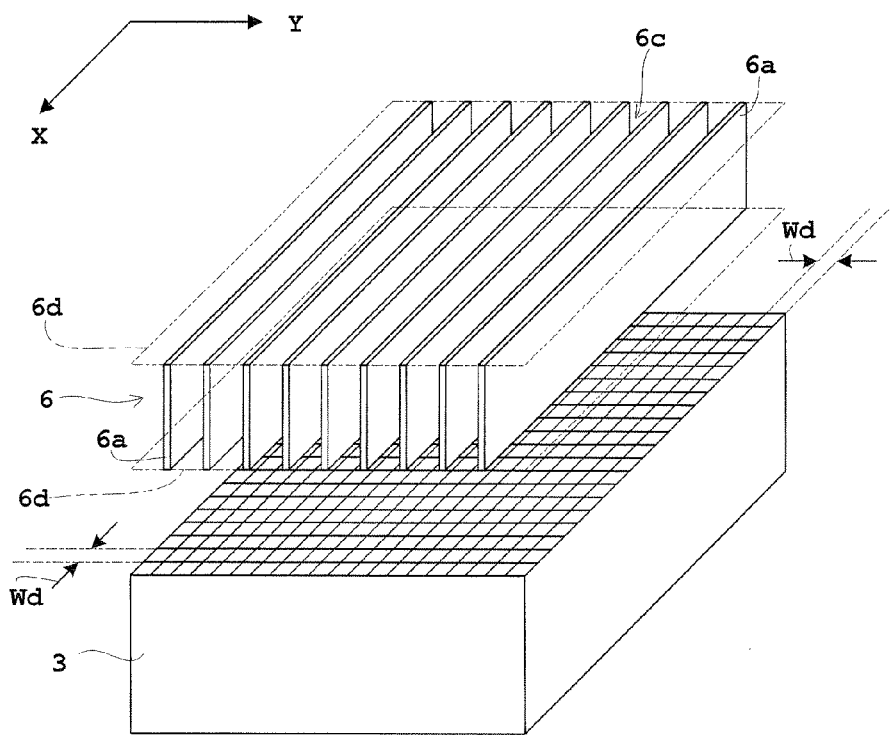
FIG. 3 is a schematic view of an air grid according to this invention.
Figure 4A:
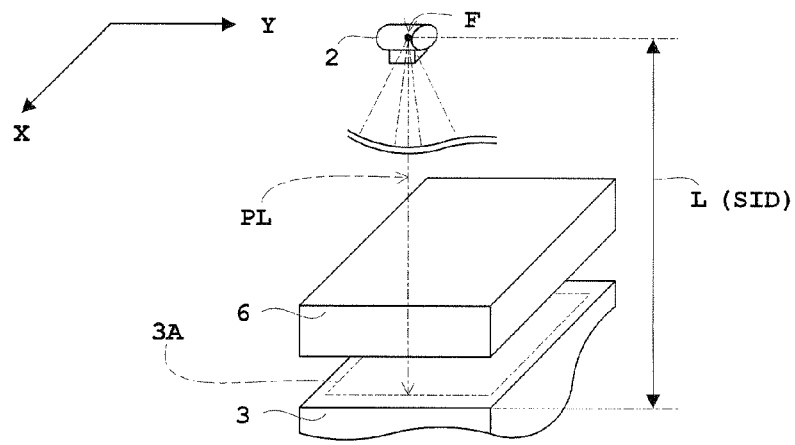
FIG. 4A is a perspective view showing an outline of the air grid and FPD together with an X-ray tube.
Figure 4B:
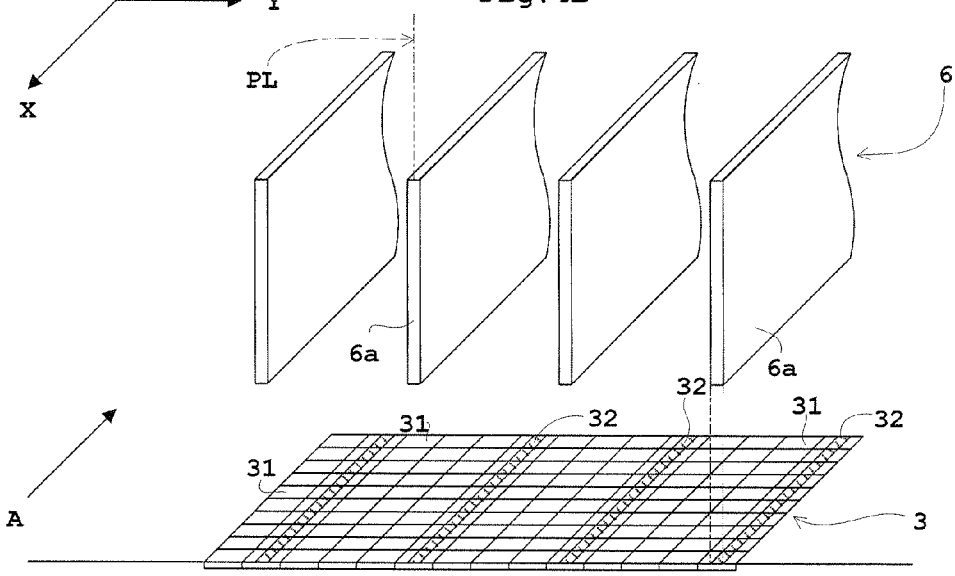
FIG. 4B is an enlarged view of peripheries of the air grid.
Figure 4C:
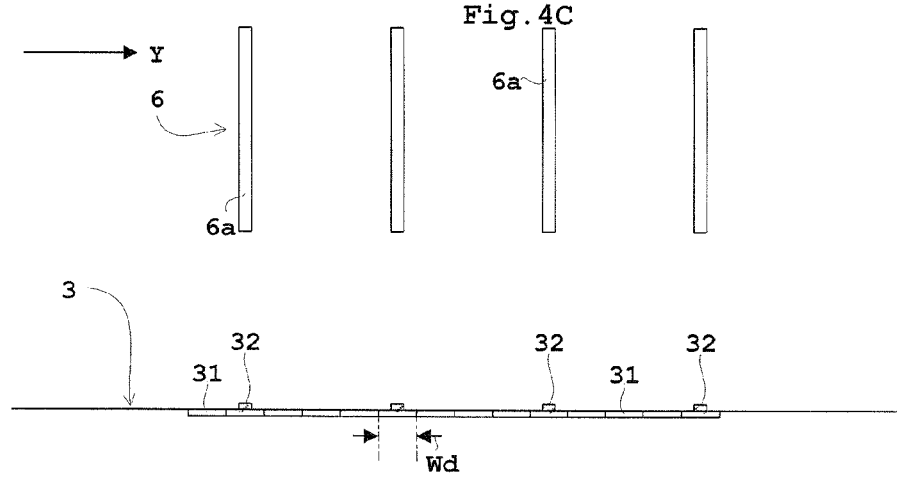
FIG. 4C is a sectional view seen from arrow A of FIG. 4B.

FIG. 1 is a block diagram of an X-ray imaging apparatus according to this invention. FIG. 2 is a schematic view of a detecting plane of a flat panel X-ray detector (FPD). FIG. 3 is a schematic view of an air X-ray grid according to this invention. FIG. 4A is a perspective view showing an outline of the air grid and FPD together with an X-ray tube. FIG. 4B is an enlarged view of peripheries of the air grid. FIG. 4C is a sectional view seen from arrow A of FIG. 4B. This embodiment will be described taking X-rays as an example of radiation.

As shown in FIG. 1, the X-ray imaging apparatus according to this invention includes a top board 1 for supporting a subject M, an X-ray tube 2 for emitting X-rays toward the subject M, a flat panel X-ray detector (hereinafter abbreviated as "FPD") 3 for detecting the X-rays emitted from the X-ray tube 2 and transmitted through the subject M, an image processor 4 for carrying out image processes based on the X-rays detected by the FPD 3, and a display 5 for displaying X-ray images having undergone the image processes by the image processor 4. The display 5 is in the form of a display device such as a monitor, television or the like. A grid 6 is attached to the detecting plane of the FPD 3. The flat panel X-ray detector (FPD) 3 corresponds to the radiation detecting device in this invention. The grid 6 corresponds to the scattered radiation removing device in this invention.

The image processor 4 includes a central processing unit (CPU) and others. The programs and the like for carrying out various image processes are written and stored in a storage medium represented by a ROM (Read-only Memory). The CPU of the image processor 4 reads from the storage medium and executes the programs and the like to carry out image processes corresponding to the programs. In particular, a grid data acquiring unit 41, a peak position calculating unit 42, a shadowless pixel calculating unit 43, a shadow total quantity calculating unit 44, an image data acquiring unit 51, a scattered component removal processing unit 52, a pixel classifying unit 53, a pixel value interpolating unit 54, a provisional transmittance calculating unit 55, a transmittance smoothing unit 56, a transmittance correcting unit 57 and an X-ray image acquiring unit 58, described hereinafter, of the image processor 4 execute programs relating to acquisition of grid data, calculation of peak positions, calculation of shadowless pixels (pixels without shadows), calculation of a total quantity of shadows, acquisition of image data, removal of scattered components (scattered X-ray components), classification of pixels, interpolation of pixel values, provisional calculation of X-ray transmittances, smoothing of the transmittances, correction of the X-ray transmittances and acquisition of a final X-ray image. In this way, the above components carry out acquisition of grid data, calculation of peak positions, calculation of shadowless pixels, calculation of a total quantity of shadows, acquisition of image data, removal of scattered components, classification of pixels, interpolation of pixel values, provisional calculation of transmittances, smoothing of the transmittances, correction of the transmittances and acquisition of an X-ray image, corresponding to the programs, respectively.

The image processor 4 includes the grid data acquiring unit 41 for acquiring grid data, the peak position calculating unit 42 for determining peak positions due to shadows, the shadowless pixel calculating unit 43 for determining pixels without shadows (shadowless pixels), the shadow total quantity calculating unit 44 for calculating a total quantity of shadows per absorbing foil strip 6a (see FIG. 3), the image data acquiring unit 51 for acquiring image data, the scattered component removal processing unit 52 for removing scattered components (scattered X-ray components) by arithmetic operation, the pixel classifying unit 53 for classifying pixels by the image data, the pixel value interpolating unit 54 for interpolating pixel values, the provisional transmittance calculating unit 55 for provisionally calculating X-ray transmittances, the transmittance smoothing unit 56 for smoothing the X-ray transmittances along a direction of extension of absorbing foil strips 6a (see FIG. 3), the transmittance correcting unit 57 for correcting the X-ray transmittances, and the X-ray image acquiring unit 58 for obtaining an X-ray image as final image data. The grid data acquiring unit 41 corresponds to the grid data acquiring device in this invention. The shadowless pixel calculating unit 43 corresponds to the shadowless pixel calculating device in this invention. The shadow total quantity calculating unit 44 corresponds to the shadow total quantity calculating device in this invention. The image data acquiring unit 51 corresponds to the first image data acquiring device in this invention. The scattered component removal processing unit 52 corresponds to the scattered component removal processing device in this invention. The pixel classifying unit 53 corresponds to the pixel classifying device in this invention. The pixel value interpolating unit 54 corresponds to the pixel value interpolating device in this invention. The provisional transmittance calculating unit 55 corresponds to the provisional transmittance calculating device in this invention. The transmittance smoothing unit 56 corresponds to the image data smoothing device in this invention. The transmittance correcting unit 57 corresponds to the image data correcting device in this invention. The X-ray image acquiring unit 58 corresponds to the second image data acquiring device in this invention.

As shown in FIG. 2, the FPD 3 has a plurality of detecting elements d sensitive to X-rays arranged in a two-dimensional matrix form on the detecting plane thereof. The detecting elements d detect X-rays by converting the X-rays transmitted through the subject M into electric signals to be stored once, and reading the electric signals stored. The electric signal detected by each detecting element d is converted into a pixel value corresponding to the electric signal. An X-ray image is outputted by allotting the pixel values to pixels corresponding to positions of the detecting elements d. The X-ray image is fed to the grid data acquiring unit 41 and image data acquiring unit 51 of the image processor 4 (see FIGS. 1 and 5). Thus, the FPD 3 has the plurality of detecting elements d arranged in rows and columns (two-dimensional matrix form) for detecting X-rays. The detecting elements d correspond to the detecting elements in this invention.

As shown in FIG. 3, the air grid 6 has absorbing foil strips 6a for absorbing scattered rays (scattered X-rays), the absorbing foil strips 6a being arranged with intermediate layers 6c in between which are voids for transmitting X-rays through. The absorbing foil strips 6a and intermediate layers 6c are covered by grid covers 6d located on an X-ray incidence plane and on an opposite plane with the absorbing foil strips 6a and intermediate layers 6c in between. In order to clarify illustration of the absorbing foil strips 6a, the grid covers 6d are shown in two-dot chain lines, and other details of the grid 6 (e.g. a structure for supporting the absorbing foil strips 6a) are not shown. The absorbing foil strips 6a correspond to the absorbing layers in this invention.

The absorbing foil strips 6a and intermediate layers 6c extending in an X-direction in FIG. 3 are arranged alternately in order in a Y-direction in FIG. 3. The X-direction in FIG. 3 is parallel to the direction of columns of detecting elements d of FPD 3 (see FIG. 2), while the Y-direction in FIG. 3 is parallel to the direction of rows of the detecting elements d of FPD 3 (see FIG. 2). Therefore, the direction of arrangement of the absorbing foil strips 6a is parallel to the rows of detecting elements d. Thus, the direction of arrangement of the absorbing foil strips 6a is the Y-direction, while the longitudinal direction (i.e. direction of extension) of the absorbing foil strips 6a is the X-direction. In summary, the direction of arrangement of the absorbing foil strips 6a (Y-direction) is parallel to the rows of the detecting element d arranged in rows and columns.

Shadows 32 of the absorbing foil strips 6a are formed on the FPD 3 (see the FIGS. 4A-4C) as a result of the absorbing foil strips 6a absorbing X-rays. The spacing between the absorbing foil strips 6a is adjusted so that the shadows 32 may be cyclically projected to every two or more pixels (four pixels in this embodiment). Where spacing of the pixels (pixel pitch) is set to Wd, the air grid 6 is constructed so that the spacing between adjacent shadows 32 may become larger than the spacing Wd of the pixels.

In this embodiment, the air grid 6 is employed as the scattered radiation removing device, with the intermediate layers 6c being void. However, the scattered radiation removing device is not limited to any particular construction, as long as the direction of arrangement of the absorbing foil strips 6a is parallel to at least either the rows or the columns of the detecting elements d, and the FPD 3 is constructed such that the shadows 32 of the absorbing foil strips 6a formed on the FPD 3 as a result of the absorbing foil strips 6a absorbing X-rays have spacing between adjacent shadows 32 larger than spacing of the pixels forming an X-ray image. For example, the absorbing foil strips 6a are not limited to any particular material, as long as a material such as lead is used which absorbs radiation represented by X-rays. As the intermediate layers 6c, instead of being void as noted above, any intermediate material such as aluminum or organic substance may be used which transmits radiation represented by X-rays.

FIGS. 4A-4C schematically show a relationship between the air grid 6 and shadows 32. As shown in FIG. 4A, sign PL is affixed to a normal extending from a focus F of X-ray tube 2 to the FPD 3, sign L is affixed to a distance (SID: Source Image Distance) of the X-ray tube 2 to the FPD 3 along the normal PL, and sign 3A is affixed to an effective field of view. As shown in FIGS. 4B and 4C, sign 31 is affixed to each pixel forming an X-ray image, and sign 32 to the shadows of the absorbing foil strips 6a.

Figure 5:
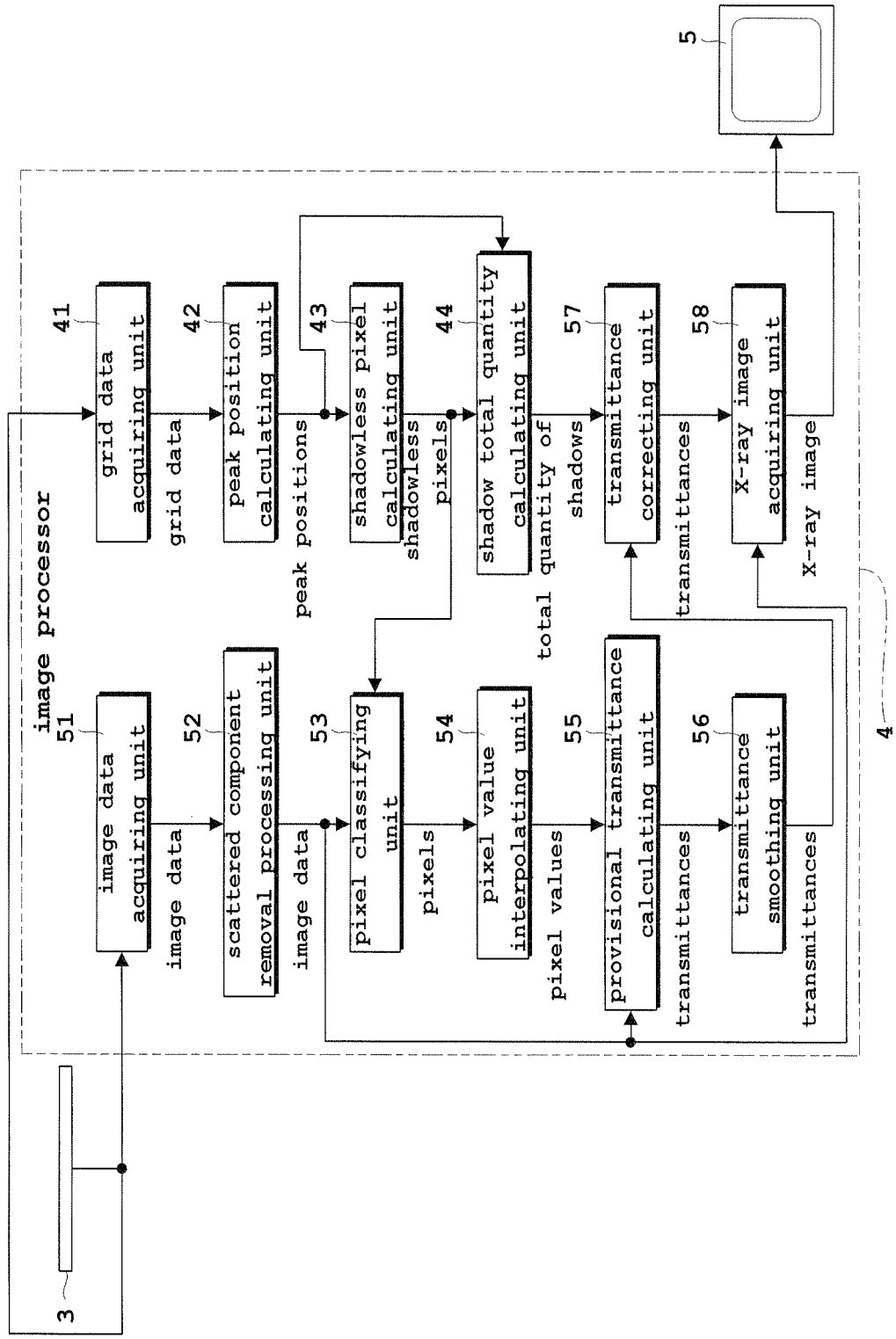
FIG. 5 is a block diagram showing a specific construction of an image processor and data flows according to this invention.
Figure 6:
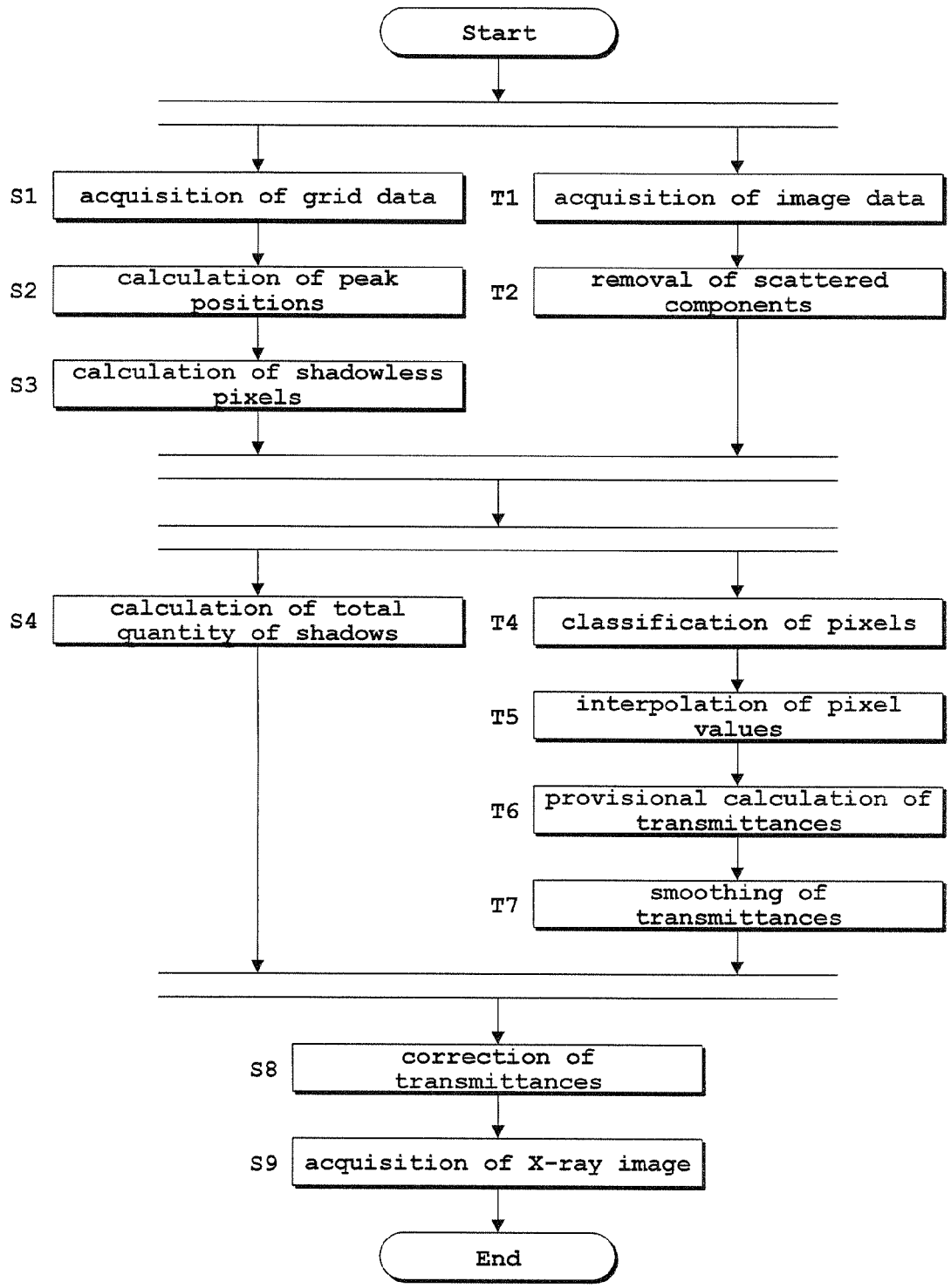
FIG. 6 is a flow chart showing a sequence of X-ray imaging according to the invention.
Figure 7:
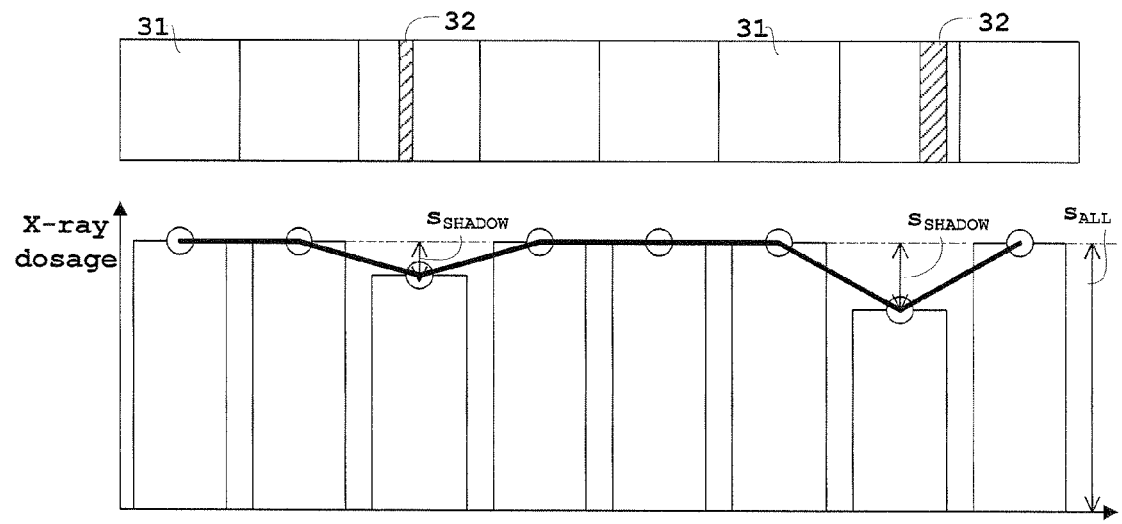
FIG. 7 is a view schematically showing a relationship between shadows and X-ray dosage.
Figure 8:
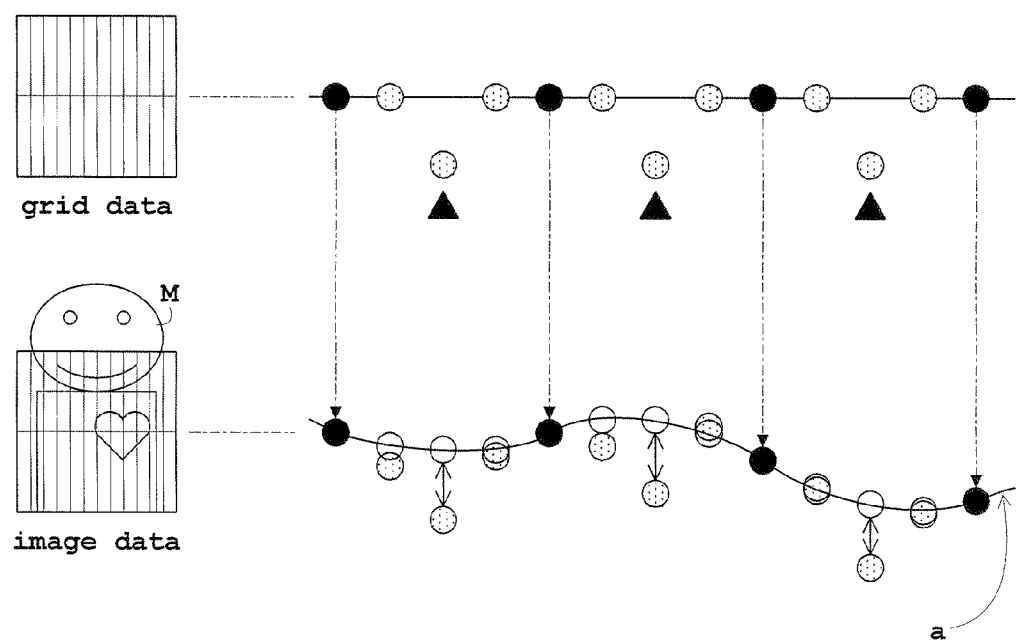
FIG. 8 is a view schematically showing a relationship between peak positions and shadowless pixels in grid data and corresponding pixels in image data.
Figure 9:
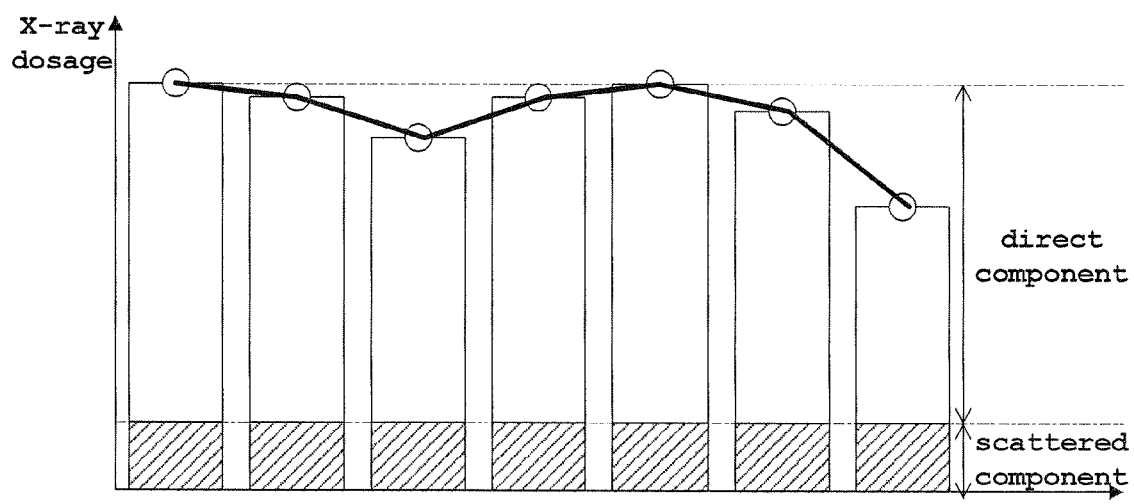
FIG. 9 is a view schematically showing X-ray dosage when scattered components are superimposed.
Figure 10A:
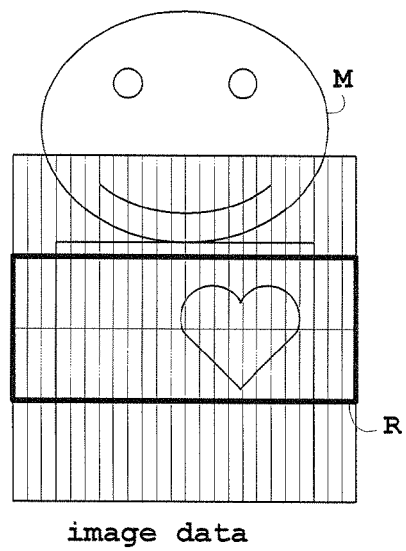
FIG. 10A is a view illustrating smoothing of X-ray transmittances.
Figure 10B:
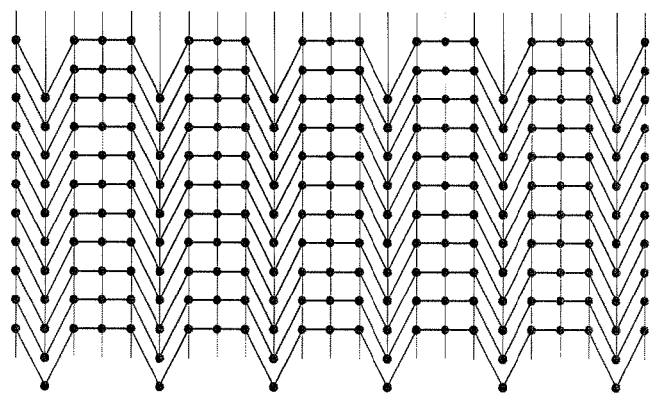
FIG. 10B is a view illustrating smoothing of X-ray transmittances.
Figure 10C:
FIG. 10C is a view illustrating smoothing of X-ray transmittances.
Figure 11:
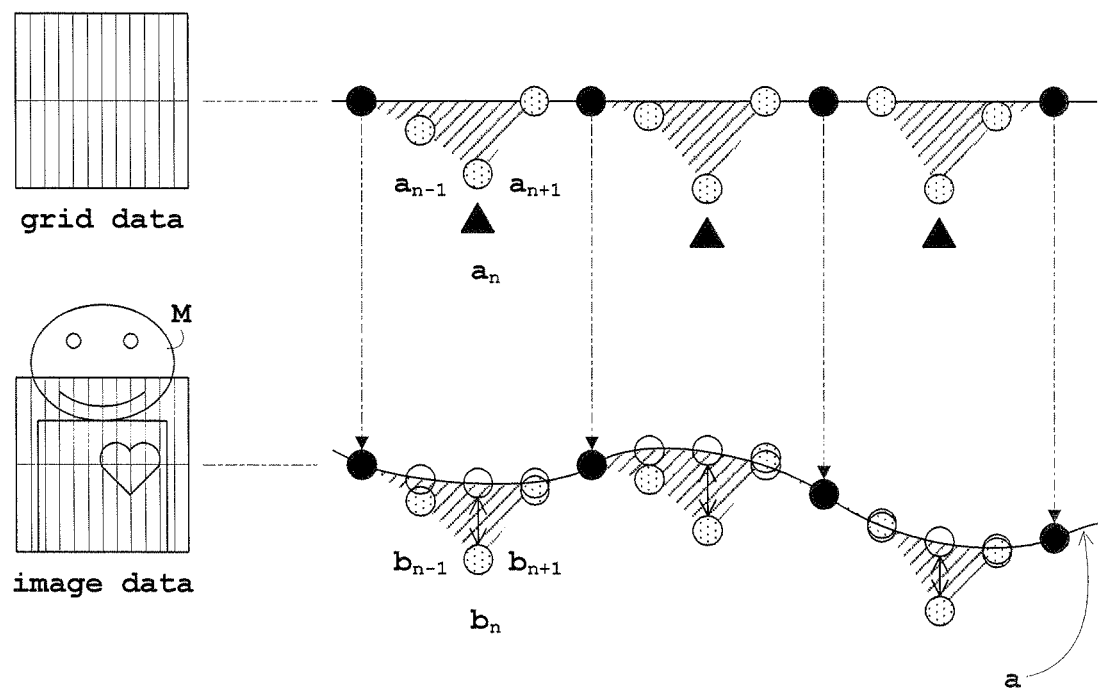
FIG. 11 is a view of a total quantity of shadows schematically applied to each pixel of the grid data and image data.
Figure 12A:
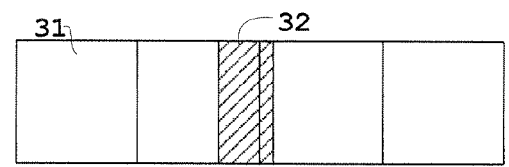
FIG. 12A is a view schematically showing an X-ray dosage and a total quantity of shadows when a shadow moves as straddling two adjacent pixels.
Figure 12A:
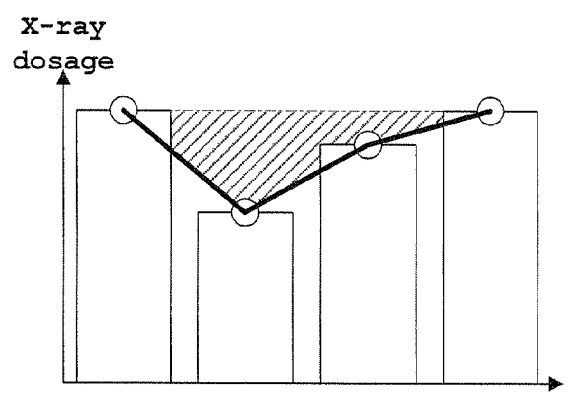
Figure 12B:
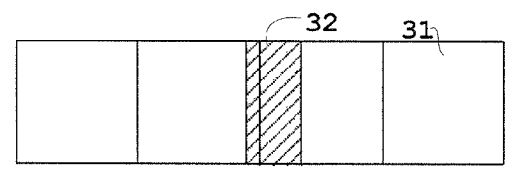
FIG. 12B is a view schematically showing the X-ray dosage and the total quantity of shadows when the shadow moves as straddling the two adjacent pixels.
Figure 12B:
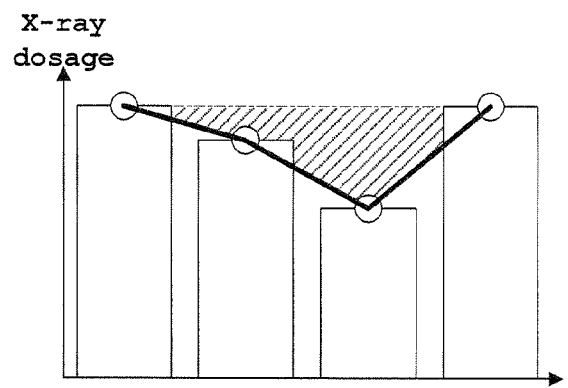
Figure 13:
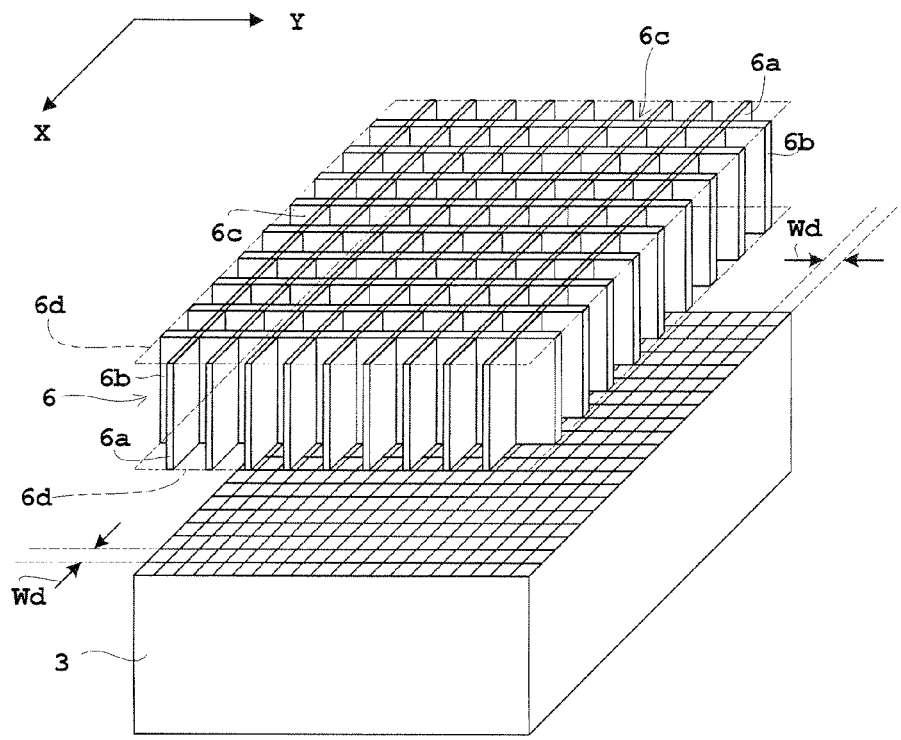
FIG. 13 is a schematic view of a cross grid in a modified embodiment.

An actual X-ray imaging and data flows according to this embodiment will be described with reference to FIGS. 5-9, FIGS. 10A-10C, FIG. 11, and FIGS. 12A and 12B. FIG. 5 is a block diagram showing a specific construction of the image processor and data flows. FIG. 6 is a flow chart showing a sequence of X-ray imaging. FIG. 7 is a view schematically showing a relationship between shadows and X-ray dosage. FIG. 8 is a view schematically showing a relationship between peak positions and shadowless pixels in grid data and corresponding pixels in image data. FIG. 9 is a view schematically showing X-ray dosage when scattered components are superimposed. FIGS. 10A-10O are views illustrating smoothing of X-ray transmittances. FIG. 11 is a view of a total quantity of shadows schematically applied to each pixel of the grid data and image data. FIGS. 12A and 12B are views schematically showing X-ray dosage and a total quantity of shadows when a shadow moves as straddling two adjacent pixels.

(Step S1) Acquisition of Grid Data

X-ray imaging is carried out in the absence of a subject and in the presence of the air grid 6 (see FIGS. 1, 3 and 4A-4C). Specifically, in the absence of a subject and in the presence of the air grid 6, X-rays are emitted from the X-ray tube 2 (see FIG. 1) toward the grid 6 and FPD 3 (see FIGS. 1-3 and 4A-4C), and the detecting elements d of the FPD 3 (see FIG. 2) read, as converted to electric signals, the X-rays transmitted through the air grid 6, and provide pixel values corresponding to the electric signals. And the FPD 3 outputs an X-ray image with an arrangement of pixel values allotted to pixels respectively corresponding to positions of the detecting elements d, and feeds the X-ray image to the grid data acquiring unit 41 as shown in FIG. 5. The grid data acquiring unit 41 acquires as grid data the X-ray image outputted in the absence of a subject and in the presence of the air grid 6. Where the SID is variable, grid data is acquired for each SID by moving the X-ray tube 2 or FPD3 by each predetermined interval (e.g. 20 mm). The grid data acquired by the grid data acquiring unit 41 is fed to the peak position calculating unit 42.

Steps S1-S3 in FIG. 6 and steps T1-T2 in FIG. 6 are executed in parallel. However, the execution of steps S1-S3 and steps T1-T2 is not limited to a particular order. Steps S1-S3 may be executed before steps T1-T2. Conversely, steps T1-T2 may be executed before steps S1-S3. Step S4 and steps T4-T7 described hereinafter may be executed in parallel as shown in FIG. 6. Step S4 may be executed before steps T4-T7, or steps T4-T7 may be executed before step S4.

Not only in the grid data, but also in the image data acquired in the presence of both a subject M (see FIG. 1) and the air grid 6, shadows 32 occur as shown in FIGS. 4A-4C and 7 as a result of the absorbing foil strips 6a of the air grid 6 (see FIG. 3) absorbing X-rays. In the grid data, an X-ray dosage immediately before incidence on the FPD 3, which is in a correspondence relation with a pixel value, is the same as before grid transmission for pixels 31 resulting from X-rays not having passed through the absorbing foil strips 6a. However, for pixels 31 having the shadows 32 projected thereto, the X-ray dosage decreases by the quantity of shadows corresponding to the quantity blocked by the absorbing foil strips 6a. As shown in FIG. 7, the larger the area of shadow 32, the less becomes the X-ray dosage and the smaller becomes the pixel value also. Conversely, the smaller the area of shadow 32, the more the X-ray dosage approaches the dosage before grid transmission. FIG. 7 shows a shadow 32 at the right having a large area, and a shadow 32 at the left having a small area. Thus, in FIG. 7, X-ray dosage is small for the shadow 32 of large area at the right, and is close to the dosage before grid transmission for the shadow 32 of small area at the left. Therefore, the X-ray dosage at pixels 31 with no shadow 32 projected thereto (see $s_{ALL}$ in FIG. 7) is proportional to pixel area, and the quantity of shadows corresponding to blockage by the absorbing foil strips 6a (see the $s_{SHADOW}$ in FIG. 7) is proportional to the area of shadow 32. Consequently, X-ray transmittance which is a ratio between the X-ray dosage before grid transmission and the X-ray dosage after grid transmission is expressed by a ratio between a pixel area and an area of a portion without shadow 32 (that is, an area obtained by subtracting an area of shadow 32 from a pixel area), as in equation (1) given hereinbefore.

(Step S2) Calculation of Peak Positions

The peak position calculating unit 42 derives peak positions due to the shadows 32 from the shadows 32 in the grid data acquired by the grid data acquiring unit 41. Specifically, as described with reference to FIGS. 4A-4C and 7, and as shown in FIG. 8, the X-ray dosage decreases at pixels 31 with shadows 32. Peak positions of the decrease are determined. In FIG. 8, the peak positions are indicated with triangles. The peak positions determined by the peak position calculating unit 42 are fed to the shadowless pixel calculating unit 43 and shadow total quantity calculating unit 44.

(Step S3) Calculation of Shadowless Pixels

The shadowless pixel calculating unit 43 determines, as a pixel without shadow 32 (shadowless pixel), a pixel 31 located in the middle between two adjacent peak positions among the peak positions provided by the peak position calculating unit 42. Specifically, as shown in FIG. 8, the location (pixel) remotest from the two peak positions can be regarded as a pixel 31 without shadow 32. Therefore, where, as in this embodiment, shadows 32 are cyclically projected to every four pixels, the pixels 31 in the middle are the shadowless pixels. Where shadows 32 are cyclically projected to every odd number of pixels, two pixels 32 are located in the middle between two adjacent peak positions. Then, one of the two middle pixels 31 is selected, and the selected pixel 31 serves as the shadowless pixel located in the middle. In FIG. 8, the shadowless pixels are indicated with black dots. The shadowless pixels determined by the shadowless pixel calculating unit 43 are fed to the shadow total quantity calculating unit 44 and pixel classifying unit 53.

(Step T1) Acquisition of Image Data

On the other hand, X-ray imaging is carried out in the presence of the subject M and air grid 6. Specifically, in the presence of the subject M and air grid 6, X-rays are emitted from the X-ray tube 2 toward the grid 6 and FPD 3, and the detecting elements d of the FPD 3 read, as converted to electric signals, the X-rays transmitted through the air grid 6, and provide pixel values corresponding to the electric signals. And the FPD 3 outputs an X-ray image with an arrangement of pixel values allotted to pixels respectively corresponding to positions of the detecting elements d, and feeds the X-ray image to the image data acquiring unit 51. The image data acquiring unit 51 acquires as image data the X-ray image outputted in the presence of the subject M and air grid 6. Where the SID is variable, image data is acquired for each SID as when the grid data is acquired in step S1. The image data acquired by the image data acquiring unit 51 is fed to the scattered component removal processing unit 52.

(Step T2) Removal of Scattered Components

Part of scattered rays from the subject M pass through the air grid 6, and scattered components (scattered X-ray components) failing to be removed by the air grid 6 may even fall on the FPD 3. Then, the scattered component removal processing unit 52 carries out a process of arithmetic operation for removing the scattered components from the image data acquired by the image data acquiring unit 51. Specifically, as shown in FIG. 9, the scattered components are superimposed on the components (direct components) of direct rays (direct X-rays), other than the scattered rays, which should finally be obtained. What is necessary is just to determine either the scattered components or the direct components, in order to remove these scattered components by arithmetic operation.

In FIG. 9, the scattered components are hatched with diagonal lines extending to the upper right.

For example, the FPD 3 detects pixel values (X-ray dosages) at three adjacent pixels 31, respectively. Each pixel value, which has become known by being detected by the FPD 3, is expressed by a sum of an unknown scattered component and a similarly unknown direct component. Unknown scattered components or unknown direct components may be determined by solving simultaneous equations for every three pixels 31, the equations expressing the pixel values by the sums of scattered components and direct components. It is preferable to select a pixel n having a shadow 32 projected thereto, and two shadowless pixels (n−1) and (n+1) adjoining the pixel n. The simultaneous equations are as follows:

$$G_{n-1}=P_{n-1}+Sc_{n+1}$$

$$G_n=P_n+Sc_n$$

$$G_{n+1}=P_{n+1}+Sc_{n+1} \quad (3)$$

where $G_{n-1}$ and $G_{n+1}$ are pixel values of the shadowless pixels (n−1) and (n+1), respectively, $G_n$ is a pixel value of the pixel n having a shadow 32 projected thereto, $Sc_{n-1}$–$Sc_{n+1}$ are scattered components at the respective pixels (n−1), n and (n+1), and $P_{n-1}$–$P_{n+1}$ are direct components at the respective pixels (n−1), n and (n+1).

When the subject M is, for example, a flat acrylic plate having a fixed thickness for direct ray transmission, direct components $P_{n-1}$–$P_{n+1}$ at the respective pixels (n−1), n and (n+1) are regarded as equal, i.e. $P_{n-1}=Pn=P_{n+1}$. Assuming that variations in the scattered components $Sc_{n-1}$-$Sc_{n+1}$ can be linearly approximated, a condition, $Sc_n=(Sc_{n+1}+Sc_{n-1})/2$, is set. Each unknown component can be determined by solving the simultaneous equations, with this condition added.

Thus, after deriving the scattered components from the above equations (3), the scattered components are removed. Alternatively, the direct components are derived from the above equations (3), and these direct components are used as image data free of the scattered components. It is not necessary to obtain pixel values of all the pixels from the above simultaneous equations (3). For example, a pixel group (three adjacent pixels) is selected at every predetermined interval, each component of the pixel group is determined by solving the simultaneous equations, and pixel values of the pixel group free of scattered components are obtained. Pixel values of the remaining pixels not selected may be obtained through an interpolating process using the pixel values of the pixel groups already obtained by solving the simultaneous equations. The interpolating process may use averages or Lagrange interpolation.

If the grid data in step S1 has already been acquired at the stage of step T2, the removing process may be carried out using the grid data also. For example, X-ray transmittance is derived from equation (1) given hereinbefore, or from the ratio between X-ray dosage before grid transmission and the X-ray dosage after grid transmission in the grid data. Each pixel value, which has become known by being detected by the FPD 3, is expressed by a sum of an unknown scattered component and a similarly unknown direct component multiplied by the transmittance. Unknown scattered components or unknown direct components may be determined by solving simultaneous equations for every three pixels, the equations expressing the pixel values by the sums of scattered components and direct components multiplied by transmittances.

The simultaneous equations are as follows:

$$G_{n+1} = P_{n+1} \cdot Cp_{n+1} + Sc_{n+1}$$

$$G_n = P_n \cdot Cp_n + Sc_n$$

$$G_{n-1} = P_{n-1} \cdot Cp_{n-1} + Sc_{n-1} \qquad (3)'$$

where $Cp_{n-1}-Cp_{n+1}$ are the transmittances at the respective pixels (n−1), n and (n+1).

The removing process can be carried out based on equations (3)' as well as the foregoing equations (3). In the case of equations (3)' above, the scattered components are removed while taking transmittance into consideration, and thus the scattered components can be removed more accurately than in the case of the foregoing equations (3). The image data from which the scattered components have been removed by the scattered component removal processing unit 52 is fed to the pixel classifying unit 53, provisional transmittance calculating unit 55 and X-ray image acquiring unit 58.

(Step T4) Classification of Pixels

The pixel classifying unit 53 classifies the pixels 31 in the image data from which the scattered components have been removed by the scattered component removal processing unit 52, into pixels 31 corresponding to the shadowless pixels in the grid data determined by the shadowless pixel calculating unit 43 and the other pixels 31. Specifically, as shown in FIG. 8, pixels 31 in the image data which are completely free of shadows 32 are determined as corresponding to the shadowless pixels in the grid data. In FIG. 8, these pixels 31 in the image data are indicated with black dots as are the shadowless pixels in the grid data, while the other pixels 31 in the image data are indicated with stipples. FIG. 8 shows, as indicated with stipples, pixels 31 other than the shadowless pixels, also including pixels 31 in the peak positions, in the grid data. The pixels 31 classified by the pixel classifying unit 53 are fed to the pixel value interpolating unit 54.

(Step T5) Interpolation of Pixel Values

Based on the pixel values of the pixels 31 corresponding to the shadowless pixels in the grid data, among the pixels 31 classified by the pixel classifying unit 53, the pixel value interpolating unit 54 interpolates pixel values of the other pixels 31. Specifically, when the subject M is a human body, and an assumption is made that variations of X-ray transmittance in the human body are not so fine in the direction of arrangement of the absorbing foil strips 6*a* as the spacing of the pixels 31 (pixel pitch), the pixels 31 in the image data corresponding to the shadowless pixels in the grid data are linked together by interpolating the pixel values of the other pixels as shown in a line "a" in FIG. 8. In FIG. 8, the pixels 31 with the interpolated pixel values are indicated with white circles. The pixel values interpolated by the pixel value interpolating unit 54 are fed to the provisional transmittance calculating unit 55.

(Step T6) Provisional Calculation of Transmittances

Based on the pixel values of the pixels 31 in the image data from which the scattered components have been removed by the scattered component removal processing unit 52, i.e. actual pixel values acquired by image pickup, and the pixel values interpolated by the pixel value interpolating unit 54, the provisional transmittance calculating unit 55 provisionally calculates X-ray transmittances. Differences between the actual pixel values acquired by image pickup and the interpolated pixel values are regarded as results of X-ray blocking (i.e. quantity of shadows) by the absorbing foil strips 6*a*, which enables a direct estimation of X-ray transmittances in the pertinent portions.

However, since the X-ray transmittances are obtained based on the actual pixel values acquired by image pickup and the interpolated pixel values, it is clear that, when the pixel values in the original image data (in this embodiment, the original image data from which the scattered components have been removed by the scattered component removal processing unit 52) are divided by the X-ray transmittances determined in this way, the results are the same as the interpolated pixel values (line "a" in FIG. 8). The line "a" in FIG. 8 represents interpolated data, and not desired data to be obtained finally. Therefore, the X-ray transmittances determined in step T6 are regarded as provisional transmittances. The X-ray transmittances in the image data provisionally calculated by the provisional transmittance calculating unit 55 are fed to the transmittance smoothing unit 56.

(Step T7) Smoothing of Transmittances

The transmittance smoothing unit 56 smoothes the X-ray transmittances in the image data provisionally calculated by the provisional transmittance calculating unit 55. Specifically, as shown in FIGS. 10A-10C, the X-ray transmittances are smoothed along the direction of extension of the absorbing foil strips 6*a*. For example, in a predetermined area R along the direction of extension of the absorbing foil strips 6*a* as shown in FIG. 10A, a plurality of transmittances belonging to the area R (see FIG. 10B) are added and averaged along the direction of extension of the absorbing foil strips 6*a*, to smooth the transmittances as shown in FIG. 10C. The smoothing may use not only the additive average (also called "arithmetic average") which adds and averages the transmittances but may use a simple addition. Any commonly used method of smoothing may be employed.

The shadows 32 of the air grid 6 hardly vary in the direction of extension of the absorbing foil strips 6*a*. On the other hand, the patterns of the subject M such as the human body are not constant in the direction of extension of the absorbing foil strips 6*a*. Therefore, when the transmittances are added and averaged along the direction of extension of the absorbing foil strips 6*a*, the influence of the human body will be canceled, and only a profile of the shadows 32 having substantially constant values will remain. This profile is called a "provisional shadow profile". As shown in FIG. 11, quantities of X-rays (quantities of shadows) in the provisional shadow profile blocked by the absorbing foil strips 6*a* are set to $b_{n-1}$, $b_n$ and $b_{+1}$ for the respective pixels (n−1), n and (n+1). A total quantity of shadows obtained from the provisional shadow profile is $b_{n-1}+b_n+b_{n+1}$. The X-ray transmittances (provisional shadow profile) in the image data smoothed by the transmittance smoothing unit 56 are fed to the transmittance correcting unit 57.

(Step S4) Calculation of Total Quantity of Shadows

On the other hand, based on the shadowless pixels obtained by the shadowless pixel calculating unit 43 and the peak positions obtained by the peak position calculating unit 42, the shadow total quantity calculating unit 44 calculates a total quantity of shadows per absorbing foil strip 6*a*. Specifically, as shown in FIG. 11, the quantity of blocked X-rays in an enclosed area including shadowless pixels and a peak position can be regarded as the total quantity of shadows per absorbing foil strip 6*a*. In FIG. 11, each enclosed area including shadowless pixels and peak position (i.e. total quantity of shadows per absorbing foil strip 6*a*) is hatched with diagonal lines extending to the upper right. The quantities of X-rays blocked by the absorbing foil strip 6*a* (quantities of shadows) are set to $a_{n-1}$, $a_n$ and $a_{n+1}$ for the respective pixels (n−1), n and (n+1). Therefore, the total quantity of shadows per absorbing foil strip 6*a* is $a_{n-1}+a_n+a_{n+1}$. The total quantity of shadows per absorbing foil strip 6a calculated by the shadow total quantity calculating unit 44 is fed to the transmittance correcting unit 57.

(Step S8) Correction of Transmittances

Figure 14A:
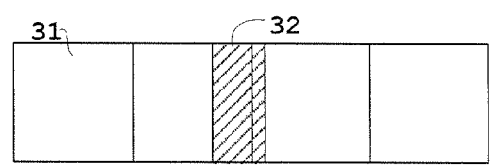
FIG. 14A is a view schematically showing a shadow moving as straddling two adjacent pixels.
Figure 14B:
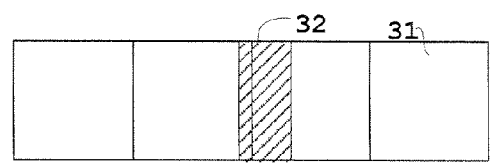
FIG. 14B is a view schematically showing the shadow moving as straddling the two adjacent pixels.

As also discussed with reference to FIGS. 14A and 14B, when a shadow 32 straddles two adjacent pixels 31 as shown in FIG. 12A and the shadow 32 moves as shown in FIG. 12B, the quantities of the shadow 32 on the pixels 31 will change. However, although the quantity of an individual shadow (i.e. the quantity of shadow for each pixel 31) changes, the total quantity of shadows per absorbing foil strip 6a should remain constant. So, on the condition that the total quantity of shadows per absorbing foil strip 6a provided by the shadow total quantity calculating unit 44 is constant, and based on the total quantity of shadows, the transmittance correcting unit 57 corrects the X-ray transmittances (provisional shadow profile) in the image data smoothed by the transmittance smoothing unit 56. Specifically, the provisional shadow profile is corrected so that the total quantity of shadows, $b_{n-1}+b_n+b_{n+1}$, obtained from the provisional shadow profile and the total quantity of shadows per absorbing foil strip 6a, $a_{n-1}+a_n+a_{n+1}$ may become the same.

This correction aims at obtaining a more accurate quantity of shadows 32, since the X-ray transmittances obtained provisionally include disturbance due to the subject to be imaged, such as the human body. Specifically, as shown in FIG. 11, a constant term k is determined to form $a_{n-1}+a_n+a_{n+1}=k\cdot(b_{n-1}+b_n+b_{n+1})$, and $k\cdot b_{n-1}$, $k\cdot b_n$ and $k\cdot b_{n+1}$ are set as new quantities of shadows for the respective pixels (n−1), n and (n+1). By carrying out such a correction, a more accurate shadow profile can be obtained from the provisional shadow profile. The X-ray transmittances are corrected by substituting the acquired shadow profile into equation (1) given hereinbefore to obtain X-ray transmittances. The X-ray transmittances corrected by the transmittance correcting unit 57 are fed to the X-ray image acquiring unit 58.

(Step S9) Acquisition of X-ray Image

Based on the X-ray transmittances corrected by the transmittance correcting unit 57, and the pixel values in the image data (actual pixel values acquired by image pickup) from which the scattered components have been removed by the scattered component removal processing unit 52, the X-ray image acquiring unit 58 calculates pixel values after shadow removal, and acquires an X-ray image having an arrangement of the pixel values after shadow removal, as final image data. Specifically, pixel values after shadow removal are obtained by substituting, into equation (2) given hereinbefore, the actual pixel values acquired by image pickup and the X-ray transmittances corrected in step S8. The X-ray image which is the final image data acquired by the X-ray image acquiring unit 58 may be outputted to the display 5, a storage medium or a printing device.

According to the X-ray imaging apparatus in this embodiment, the air grid 6 is constructed such that the absorbing foil strips 6a, which absorb scattered X-rays (scattered rays), are arranged in a direction parallel to at least one of the directions of the rows and columns of detecting elements d (parallel to the direction of the rows in FIG. 3), and that the spacing between adjacent shadows 32 among the shadows 32 of the absorbing foil strips 6a formed on the flat panel X-ray detector (FPD) 3 as a result of the absorbing foil strips 6a absorbing X-rays is larger than the spacing between the pixels 31 forming an X-ray image. With this construction, pixels 31 without shadows 32 (shadowless pixels) appear in every row or column (column in FIG. 3) of detecting elements d parallel to the direction of arrangement of the absorbing foil strips 6a. Therefore, the grid data acquiring unit 41 acquires grid data in the absence of a subject and in the presence of the air grid 6, and the peak position calculating unit 42 calculates peak positions of shadows 32 based on the shadows 32 in the grid data acquired by the grid data acquiring unit 41. The shadowless pixel calculating unit 43 determines, as a pixel 31 without shadow 32 (shadowless pixel), a pixel 31 located in the middle between two adjacent peak positions among the peak positions calculated by the peak position calculating unit 42. At this time, the pixels 31 without shadows 32 which actually appear, and the pixels 31 without shadows 32 determined are substantially in agreement. The shadow total quantity calculating unit 44 calculates a total quantity of shadows per absorbing foil strip 6a, based on the pixels 31 without shadows 32 provided by the above shadowless pixel calculating unit 43 and the peak positions provided by the above peak position calculating unit 42. That is, the quantity of blocked X-rays in enclosed areas including the shadowless pixels and peak positions can be regarded as the total quantity of shadows per absorbing foil strip 6a.

On the other hand, the image data acquiring unit 51 acquires image data in the presence of the subject M and air grid 6. The transmittance smoothing unit 56 smoothes the image data acquired by the image data acquiring unit 51 (in this embodiment, the image data from which the scattered components have been removed by the scattered component removal processing unit 52) along the direction of extension of the absorbing foil strips 6a. Consequently, the influence of the subject M is canceled from the image data smoothed by the transmittance smoothing unit 56, and only the profile of shadows 32 having a substantially constant value remains therein. Therefore, the image data smoothed by the transmittance smoothing unit 56 includes only the profile of shadows 32, with the influence of the subject M canceled, while retaining the data of the subject M.

Even when a shadow 32 straddles a plurality of pixels 31 or the shadow position moves relative to the pixels 31, the total quantity of shadows per absorbing foil strip 6a can be regarded as constant. So, on the condition that the total quantity of shadows per absorbing foil strip 6a provided by the shadow total quantity calculating unit 44 is constant, and based on the total quantity of shadows, the transmittance correcting unit 57 corrects the image data smoothed by the transmittance smoothing unit 56. This correction can cancel the disturbance by the subject M, to provide a profile of shadows 32 at an actual time of X-ray image pickup of the subject M. Therefore, even when a shadow 32 straddles a plurality of pixels 31 or the shadow position moves relative to the pixels 31, the X-ray image acquiring unit 58 can determine data after shadow removal, based on the image data corrected by the above transmittance correcting unit 57 and the image data acquired by the above image data acquiring unit 51 (in this embodiment, the image data from which the scattered components have been removed by the scattered component removal processing unit 52), and acquire the data after shadow removal as final image data. As a result, the shadow removal can be carried out with high accuracy by using the corrected image data which is the profile of shadows 32 at an actual time of X-ray image pickup of the patient M.

This embodiment specifies X-ray transmittances in the image data acquired by the image data acquiring unit 51. And the transmittance smoothing unit 56 and transmittance correcting unit 57 carry out processes on the X-ray transmittances, respectively. For this purpose, X-ray transmittances are determined provisionally.

First, the pixel classifying unit 53 classifies the pixels 31 in the image data acquired by the image data acquiring unit 51 (in this embodiment, the image data from which the scattered components have been removed by the scattered component removal processing unit 52), into pixels 31 corresponding to the pixels 31 without shadows 32 (shadowless pixels) in the grid data determined by the shadowless pixel calculating unit 43 and the other pixels 31. Through this classification, the shadowless pixels in the grid data can be applied to the pixels 31 in the image data corresponding to the shadowless pixels. Then, based on the pixel values of the pixels 31 corresponding to the shadowless pixels in the grid data, among the pixels 31 classified by the pixel classifying unit 53, the pixel value interpolating unit 54 interpolates pixel values of the other pixels 31. That is, when an assumption is made that variations of X-ray transmittance in the subject M are not so fine (in the direction of arrangement of the absorbing foil strips 6a) as the spacing of the pixels 31 (pixel pitch), the pixels 31 in the image data corresponding to the shadowless pixels in the grid data are linked together by interpolating the pixel values of the other pixels.

Then, based on the image data acquired by the image data acquiring unit 51 (in this embodiment, the image data from which the scattered components have been removed by the scattered component removal processing unit 52) and the pixel values interpolated by the pixel value interpolating unit 54, the provisional transmittance calculating unit 55 provisionally calculates X-ray transmittances. That is, differences between the actual pixel values acquired by image pickup and the interpolated pixel values are regarded as results of X-ray blocking by the absorbing foil strips 6a, which enables a direct estimation of X-ray transmittances in the pertinent portions.

However, as noted hereinbefore, since the X-ray transmittances are obtained based on the actual pixel values acquired by image pickup and the interpolated pixel values, it is clear that, when the pixel values in the original image data are divided by the X-ray transmittances determined in this way, the results are the same as the interpolated pixel values. Therefore, by regarding the obtained X-ray transmittances as provisional transmittances, the transmittance smoothing unit 56 smoothes the X-ray transmittances in the image data provisionally obtained by the provisional transmittance calculating unit 55. The transmittance correcting unit 57 corrects the X-ray transmittances in the image data smoothed by the transmittance smoothing unit 56, based on the total quantity of shadows. Based on the X-ray transmittances in the image data corrected by the transmittance correcting unit 57, and the pixel values in the image data acquired by the image data acquiring unit 51 (in this embodiment, the image data from which the scattered components have been removed by the scattered component removal processing unit 52), the X-ray image acquiring unit 58 can calculate pixel values after shadow removal, and acquire an X-ray image having an arrangement of the pixel values after shadow removal, as final image data. As a result, the shadow removal can be carried out with high accuracy by using the corrected X-ray transmittances which constitute a profile of shadows 32 at an actual time of X-ray image pickup of the subject M.

This embodiment provides the scattered component removal processing unit 52 as a desired element in case part of the scattered X-rays (scattered rays) from the subject M pass through the air grid 6, thus failing to be removed by the air grid 6.

That is, the scattered component removal processing unit 52 is provided for removing, by arithmetic operation, scattered ray components (scattered components) of the image data acquired by the image data acquiring unit 51, which components have failed to be removed by the air grid 6. The X-ray image acquiring unit 58 acquires final image data based on the image data from which the scattered components have been removed by the scattered component removal processing unit 52.

The scattered components are removed by arithmetic operation as above, and the image data acquired by the image data acquiring unit 51 is replaced with the image data from which the scattered components have been removed by the scattered component removal processing unit 52. Thus, the shadow removal can be carried out with high accuracy, while removing the scattered components.

This invention is not limited to the foregoing embodiment, but may be modified as follows:

(1) The foregoing embodiment has been described taking X-rays as an example of radiation. However, the invention is applicable to radiation other than X-rays (such as gamma rays).

(2) In the foregoing embodiment, the radiographic apparatus is constructed for medical use to conduct radiography of a patient placed on the top board 1 as shown in FIG. 1. This is not limitative. For example, the apparatus may be constructed like a nondestructive testing apparatus for industrial use which conducts radiography of an object (in this case, a subject tested) conveyed on a belt, or may be constructed like an X-ray CT apparatus for medical use.

(3) The foregoing embodiment employs an air grid as the scattered radiation removing device represented by a grid, but the grid is not limited to the air grid. The grid may have, in place of the voids, an intermediate material such as aluminum or organic substance which transmits radiation represented by X-rays. Further, a cross grid may be employed as shown in FIG. 11. Specifically, while the absorbing foil strips 6a and intermediate layers 6c extending in the X-direction in FIG. 3 are arranged alternately in order in the Y-direction in FIG. 3, absorbing foil strips 6b and intermediate layers 6c extending in the Y-direction in FIG. 3 are arranged alternately in order in the X-direction in FIG. 3, such that the absorbing foil strips 6a and absorbing foil strips 6b cross one another. The X-direction in FIG. 3 is parallel to the rows of detecting elements d of FPD 3 (see FIG. 2), while the Y-direction in FIG. 3 is parallel to the columns of detecting elements d of FPD 3 (see FIG. 2). Therefore, the directions of arrangement of the absorbing foil strips 6a and 6b are parallel to both the rows and columns of detecting elements d of FPD 3.

(4) In the foregoing embodiment, the scattered radiation removing device (air grid 6 in the embodiment) is constructed to project the shadows 32 cyclically to every four pixels 31. The construction is not limited to this, but may be modified, for example, to project the shadows 32 cyclically to every two pixels 31 or every three pixels 31.

(5) The foregoing embodiment provides the scattered component removal processing device (scattered component removal processing unit 52 in the embodiment) for removing, by arithmetic operation, any scattered radiation (scattered X-rays in the embodiment) having failed to be removed by the scattered radiation removing device (air grid 6 in the embodiment). Where such scattered radiation is negligible or there is no need to consider scattered radiation, it is not absolutely necessary to provide the scattered component removal processing device (scattered component removal processing unit 52). Where no scattered component removal processing device (scattered component removal processing unit 52) is provided, the image data acquired by the first image data acquiring device (image data acquiring unit 51 in the embodiment) may be used directly in the processes by the pixel classifying device (pixel classifying unit 53 in the embodiment), provisional transmittance calculating device (provisional transmittance calculating unit 55 in the embodiment), image data smoothing device (transmittance smoothing unit 56 in the embodiment) and second image data acquiring device (X-ray image acquiring unit 58 in the embodiment).

(6) The foregoing embodiment specifies X-ray transmittances in the image data acquired by the first image data acquiring device (image data acquiring unit 51 in the embodiment). The image data smoothing device (transmittance smoothing unit 56 in the embodiment) and image data correcting device (transmittance correcting unit 57 in the embodiment) carry out processes on the X-ray transmittances, respectively. An example of image data is not limited to the transmittances as in the embodiment. For example, the above devices may carry out the processes on pixel values of the direct components, or on the scattered components.

This invention may be embodied in other specific forms without departing from the spirit or essential attributes thereof and, accordingly, reference should be made to the appended claims, rather than to the foregoing specification, as indicating the scope of the invention.

What is claimed is:

1. A radiographic apparatus for obtaining a radiological image, comprising:
    a scattered radiation removing device for removing scattered radiation; and
    a radiation detecting device having a plurality of detecting elements arranged in rows and columns for detecting radiation;
    the scattered radiation removing device being constructed to have absorbing layers for absorbing the scattered radiation, which layers are arranged in a direction parallel to at least one of directions of rows and columns of the detecting elements, such that spacing between adjacent shadows among shadows of the absorbing layers formed on the radiation detecting device as a result of the absorbing layers absorbing the radiation is larger than spacing between pixels forming the radiological image;
    the apparatus further comprising:
    a first image data acquiring device for acquiring image data in presence of a subject to be imaged and the scattered radiation removing device;
    an image data smoothing device for smoothing the image data acquired by the first image data acquiring device, along a direction of extension of the absorption layers;
    a grid data acquiring device for acquiring grid data in absence of the subject and in presence of the scattered radiation removing device;
    a shadowless pixel calculating device for obtaining pixels without shadows based on the shadows in the grid data acquired by the grid data acquiring device;
    a shadow total quantity calculating device for calculating a total quantity of shadows per absorbing layer based on positions of the pixels without shadows obtained by the shadowless pixel calculating device;
    an image data correcting device for correcting the image data smoothed by the image data smoothing device, based on the total quantity of shadows per absorbing layer calculated by the shadow total quantity calculating device; and
    a second image data acquiring device for determining data after shadow removal based on the image data corrected by the image data correcting device and the image data acquired by the first image data acquiring device, and acquiring the data after shadow removal as final image data.

2. The radiographic apparatus according to claim 1, further comprising:
    a pixel classifying device for classifying pixels in the image data acquired by the first image data acquiring device, into pixels corresponding to the pixels without the shadows in the grid data obtained by the shadowless pixel calculating device, and other pixels;
    a pixel value interpolating device for interpolating pixel values of the other pixels, based on pixel values of the pixels corresponding to the pixels without the shadows in the grid data, among the pixels classified by the pixel classifying device; and
    a provisional transmittance calculating device for provisionally calculating transmittances of the radiation based on the pixel values of the pixels in the image data acquired by the first image data acquiring device and the pixel values interpolated by the pixel value interpolating device;
    wherein the image data smoothing device is arranged to smooth the transmittances of the radiation in the image data provisionally calculated by the provisional transmittance calculating device;
    the image data correcting device is arranged to correct the transmittances of the radiation in the image data smoothed by the image data smoothing device based on the total quantity of shadows; and
    the second image data acquiring device is arranged to determine pixel values after shadow removal based on the transmittances of the radiation in the image data corrected by the image data correcting device and pixel values in the image data acquired by the first image data acquiring device, and to acquire the radiological image with an arrangement of the pixel values after shadow removal as final image data.

3. The radiographic apparatus according to claim 1, further comprising a scattered component removal processing device for removing, by arithmetic operation, scattered radiation components of the image data acquired by the first image data acquiring device, which components have failed to be removed by the scattered radiation removing device, wherein the second image data acquiring device is arranged to acquire the final image data based on the image data from which the scattered radiation components have been removed by the scattered component removal processing device.

4. The radiographic apparatus according to claim 3, wherein the scattered component removal processing device is arranged to express known pixel values with sums of the scattered radiation components which are unknown and similarly unknown direct radiation components, and to determine the unknown scattered radiation components or the unknown direct radiation components by solving simultaneous equations expressing the pixel values with the sums of the scattered radiation components and the direct radiation components.

5. The radiographic apparatus according to claim 4, wherein a pixel n having a shadow projected thereto and two shadowless pixels (n−1) and (n+1) adjoining the pixel n are selected, which are expressed by simultaneous equations below:

$$G_{n-1} = P_{n-1} + Sc_{n+1}$$

$$G_n = P_n + Sc_n$$

$$G_{n+1} = P_{n+1} + Sc_{n+1} \qquad (3)$$

where $G_{n-1}$ and $G_{n+1}$ are pixel values of the shadowless pixels (n−1) and (n+1), respectively, $G_n$ is a pixel value of the pixel n having a shadow projected thereto, $Sc_{n-1}$, $Sc_n$ and $Sc_{n+1}$ are the scattered radiation components at the respective pixels (n−1), n and (n+1), and $P_{n-1}$, $P_n$ and $P_{n+1}$ are the direct radiation components at the respective pixels (n−1), n and (n+1).

6. The radiographic apparatus according to claim 5, wherein, when a thickness for transmitting the direct radiation components is fixed, a condition $P_{n-1}=P_n=P_{n+1}$ is set by regarding the direct radiation components $P_{n-1}$, $P_n$ and $P_{n+1}$ at the respective pixels (n−1), n and (n+1) as equal.

7. The radiographic apparatus according to claim 5, wherein a condition $Sc_n=(Sc_{n+1}+Sc_{n-1})/2$ is set by assuming that variations in the scattered radiation components $Sc_{n-1}$, $Sc_n$ and $Sc_{n+1}$ at the respective pixels n−1), n and (n+1) can be linearly approximated.

8. The radiographic apparatus according to claim 4, wherein a pixel group is selected at every predetermined interval, each component of the pixel group is determined by solving the simultaneous equations, and pixel values of the pixel group free of the scattered radiation components are obtained, pixel values of remaining pixels not selected being obtained through an interpolating process using the pixel values of the pixel group already obtained by solving the simultaneous equations.

9. The radiographic apparatus according to claim 8, wherein the interpolating process uses averages.

10. The radiographic apparatus according to claim 8, wherein the interpolating process uses Lagrange interpolation.

11. The radiographic apparatus according to claim 3, wherein:
   the transmittances of the radiation are derived from transmittance of radiation=(pixel area−shadow area)/pixel area, or from a ratio between a radiation dosage before transmission through the scattered radiation removing device and a radiation dosage after transmission through the scattered radiation removing device in the grid data; and
   the scattered component removal processing device is arranged to express known pixel values with sums of the scattered radiation components which are unknown and similarly unknown direct radiation components multiplied by the transmittances, and to determine the unknown scattered radiation components or the unknown direct radiation components by solving simultaneous equations expressing the pixel values with the sums of the scattered radiation components and the direct radiation components multiplied by the transmittances.

12. The radiographic apparatus according to claim 11, wherein a pixel n having a shadow projected thereto and two shadowless pixels (n−1) and (n+1) adjoining the pixel n are selected, which are expressed by simultaneous equations below:

$$G_{n+1}=P_{n+1}\cdot Cp_{n+1}+Sc_{n+1}$$

$$G_n=P_n\cdot Cp_n+Sc_n$$

$$G_{n-1}=P_{n-1}\cdot Cp_{n-1}+Sc_{n-1} \qquad (3)'$$

where $G_{n-1}$ and $G_{n+1}$ are pixel values of the shadowless pixels (n−1) and (n+1), respectively, $G_n$ is a pixel value of the pixel n having a shadow projected thereto, $Sc_{n-1}$, $Sc_n$ and $Sc_{n+1}$ are the scattered radiation components at the respective pixels (n−1), n and (n+1), $P_{n-1}$, $P_n$ and $P_{n+1}$ are the direct radiation components at the respective pixels (n−1), n and (n+1), and $Cp_{n-1}$, $Cp_n$ and $Cp_{n+1}$ are the transmittances at the respective pixels (n−1), n and (n+1).

13. The radiographic apparatus according to claim 1, further comprising a peak position calculating device for calculating peak positions of the shadows, wherein the shadowless pixel calculating device is arranged to obtain the pixels without the shadows, based on the peak positions calculated by the peak position calculating device.

14. The radiographic apparatus according to claim 13, wherein the shadowless pixel calculating device is arranged to obtain, as one of the pixels without the shadows, a middle pixel between two adjacent peak positions among the peak positions calculated by the peak position calculating device.

15. The radiographic apparatus according to claim 13, wherein, when the shadows are cyclically projected to every odd number of pixels, the shadowless pixel calculating device is arranged to select one of two middle pixels between two adjacent peak positions among the peak positions calculated by the peak position calculating device, and to obtain the selected one of the two middle pixels as one of the pixels without the shadows.

* * * * *